United States Patent [19]

Frangatos

[11] 4,229,310

[45] Oct. 21, 1980

[54] LUBRICANT COMPOSITIONS

[75] Inventor: Gerassimos Frangatos, Cherry Hill, N.J.

[73] Assignee: Mobil Oil Corporation, New York, N.Y.

[21] Appl. No.: 887,396

[22] Filed: Mar. 16, 1978

[51] Int. Cl.³ .............................................. C10M 1/46
[52] U.S. Cl. ................... 252/49.9; 252/49.8; 260/952; 260/974
[58] Field of Search ............................. 252/49.8, 49.9; 260/952, 974

[56] References Cited

U.S. PATENT DOCUMENTS

| | | | |
|---|---|---|---|
| 3,215,720 | 11/1965 | Atwood et al. | 260/952 X |
| 3,558,491 | 1/1971 | Fowler et al. | 260/49.8 |
| 4,077,892 | 3/1978 | Frangatos | 252/49.8 X |

FOREIGN PATENT DOCUMENTS 682442  11/1952  United Kingdom ................ 252/49.8

*Primary Examiner*—Andrew Metz
*Attorney, Agent, or Firm*—Charles A. Huggett; Raymond W. Barclay; Claude E. Setliff

[57] ABSTRACT

The invention provides a lubricant additive and a lubricant composition having improved demulsifying and anti-wear properties resulting from the addition thereto of such additive, which is made by reacting a partially esterified multifunctional alcohol with a phosphorus oxyhalide or a trihydrocarbyl phosphate.

16 Claims, No Drawings

LUBRICANT COMPOSITIONS

BACKGROUND OF THE INVENTION

1. Field of the Invention

The invention relates to improving the antiwear and demulsifying properties of a lubricant. More particularly it is concerned with improving such properties by adding to the lubricant a small amount of a phosphorus-containing compound.

2. Description of the Prior Art

Lubricants are subject to heavy stresses that can affect their antiwear and load carrying ability. Thus, there has been considerable effort to discover class of compounds that will aid in retaining or, preferably, in improving these important properties.

For example, sulfur compounds have been used for the purpose, as is taught in U.S. Pat. No. 3,697,499. Unfortunately, the presence of sulfur in lubricants may cause severe metal corrosion, especially copper. To overcome this, special processes have been used to moderate the effect of sulfur as in U.S. Pat. No. 3,697,499, or other materials have been used, among them certain phosphorus compounds as lubricant additives. U.S. Pat. No. 3,663,439, for instance, discloses lubricating oils where extreme pressure properties have been improved by adding thereto a reaction product involving a trihydrocarbyl phosphite.

SUMMARY OF THE INVENTION

In accordance with the invention there is provided a lubricant composition comprising lubricant and an antiwear or demulsifying amount of a product made by reacting a partially esterified polyfunctional alcohol with a phosphorus oxyhalide, e.g. the chloride, or a trihydrocarbyl phosphate. The lubricant composition may also contain other additives.

DESCRIPTION OF SPECIFIC EMBODIMENTS

Due to the complex nature of the reaction that occurs between the partially esterified material and the phosphorus compounds specified, no precise structure can be applied to the reaction product. Thus, the final product will be referred to herein, both in the specification and claims, as a product of the specified reaction.

The partially esterified products useful in the practice of this invention are those prepared from polyhydric alcohols and monocarboxylic acids. The polyhydric alcohols may contain from 2 to 20 carbon atoms and from 2 to 12 hydroxyl groups, preferably 2 to 6 and more preferably 2 to 4. Illustrative of the useful materials are (1) the trimethylols, such as the ethane, propane and butane derivatives, (2) 2,2-disubstituted propane diols, (3) pentaerythritols and certain sugars and dissacharides.

The acids used in the esterification reaction are the monocarboxylic acids containing from 4 to 20 carbon atoms. Preferably the acid is an aliphatic acid and more preferably one containing from 5 to 9 carbon atoms. Thus, the more preferred acids include the valeric, caproic, heptanoic, caprylic and pelargonic acids and mixtures thereof.

The partially esterified products are prepared by reacting at least 1 mole of the acid with each mole of the polyfunctional alcohol, but less of the acid than would be stoichiometrically required to react with all hydroxyl functions. For instance, for a dihydric alcohol, one mole of acid would be required.

In general, the reaction can be carried out at from about 120° C. to about 225° C., preferably from about 160° C. to about 185° C. The temperature, of course, is selected in accordance with the alcohol and/or acid used. Times will vary also depending upon the reactants. These will vary from about 1 hour to about 6 hours and will preferably be from about 1 hour to about 2 hours. Solvents may be used if desired to facilitate the azeotropic removal of the water formed during the esterification reaction and to facilitate reaction through solution of the reactants. When used, the solvent should be removed, so it should be selected not only for its ability to solubilize the reactants and the product of reaction, but also for its ease of separation from the reaction medium. When a solvent is not used, it is recommended that any insolubles be removed by filtration or other means.

In another aspect of the invention, the partially esterified product can be prepared by heating together a mixture of ester, i.e., the completely esterified product, and the alcohol used to prepare such ester. For example, such partial ester can be prepared by heating together a mixture of an ester made from pentaerythritol and a $C_5$-$C_9$ aliphatic monocarboxylic acid and pentaerythritol. For this reaction, a molar ratio of ester to alcohol of from 1:1 to 3:1 can be used. In carrying out the reaction it is advantageous to use a basic catalyst such as calcium hydroxide.

The reaction temperatures for this aspect will vary, ranging from about 150° C. to about 225° C., preferably from about 200° C. to about 225° C. Times to assure complete reaction between the ester and alcohol will range from about 1 hour to about 6 hours, preferably from about 2 hours to about 4 hours.

As has already been stated, the partially esterified product, obtained by either of the above methods, may be reacted with a phosphorus oxyhalide, including phosphorus oxychloride and oxybromide, which are used in amounts stoichiometrically equivalent to the hydroxyl remaining in the partial ester. The presence of a base, such as tertiary amine, as an acid carrier is desirable, because without it the acid may cleave some of the —P—OR moieties to form free —P—OH groups. Nitrogen may also be sparged through the reaction mixture. Reaction temperatures will vary from about 0° C. to about 75° C., preferably about 25° C. to about 75° C. The reaction is carried out until completion, usually requiring from about 10 minutes to about 2 hours, preferably from about 30 minutes to about 1 hour.

The trihydrocarbyl phosphates that may be reacted with the partially esterified product have the formula:

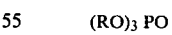

(RO)$_3$ PO where R may be the same or different and is a hydrocarbyl group containing from 1 to 6 carbon atoms. The phosphates wherein R is a lower alkyl, i.e., an alkyl having from 1 to 6 carbon atoms, are preferred. The useful reactants include those phosphates wherein R in the formula is methyl, ethyl, butyl or hexyl. This reactant is employed to the extent of from about 0.25 mole to about 3 moles thereof, preferably about 1 mole to about 2 moles, per mole of partially esterified product. The time reaction will vary from about 1 hour to about 6 hours, preferably about 2 hours to about 4 hours and will be conducted at a temperature within the range of from about 125° C. to about 225° C., preferably about 180° to about 200° C.

The lubricants which may be used with the reaction products of this invention are mineral and synthetic lubricating oils and greases therefrom. The mineral oils will be understood to include not only the paraffinic members, but also the naphthenic members. By synthetic oils are meant synthetic hydrocarbons, polyalkylene oxide oils, polyacetals, polysilicones and the like, as well as synthetic ester oils. Included among the latter type are those esters made from monohydric alcohols and polycarboxylic acids, such as 2-ethyl-hexylazelate and the like. Also included are those esters made from polyhydric alcohols and aliphatic monocarboxylic acids. Those of this group are especially important and in this group are found esters prepared from (1) the trimethylols, such as the ethane, propane and butane derivatives thereof, (2) 2,2-disubstituted propane diols and (3) the pentaerythritols reacted with aliphatic monocarboxylic acids containing from about 4 to 9 carbon atoms. Mixtures of these acids may be used to prepare the esters. Preferred among the esters are those made from pentaerythritol and a mixture of $C_5$-$C_9$ acids.

As has been indicated, the reaction products disclosed herein are useful as antiwear and demulsifying agents, this latter utility being connected with oil-in-water and water-in-oil emulsions. When so used, they may be added in amounts sufficient to impart such properties to the lubricant. More particularly, such properties will be imparted to the lubricant by adding from about 0.01% to about 10% by weight, preferably from about 0.01% to about 3%, of the neat product.

Having discussed the invention in broad and general terms, the following are offered to illustrate it. It is to be understood that the examples are merely illustrative and are not intended to limit the scope of the invention.

EXAMPLE 1

A mixture of 103.5 g (0.75 mole) of pentaerythritol, 195 g (1.5 moles) of heptanoic acid and 2 g of p-toluenesulfonic acid was heated to 175° C. with stirring under a nitrogen atmosphere. Heating was continued until 27 ml (the theoretical amount) of water was collected. 91 g (0.5 mole) of triethyl phosphate was added and the mixture was heated at 200°-205° C. with stirring. 66 g of ethanol was collected during the heating period. 278 g of clear yellowish oil was collected as the product.

EXAMPLE 2

To the mixture of Example 1, after heating at 175° C., there was added 151.5 g (1.5 mole) of triethylamine and 500 ml of cyclohexane. The reaction mixture was cooled to 5° C. and 76.6 g (0.5 mole) of phosphorus oxychloride was added over a period of 30 minutes with stirring and external cooling to maintain 5° C. The reaction mixture was subsequently brought to reflux temperature (about 80° C.) and kept there for 2 hours, after which it was cooled and filtered. The solids were dissolved in 300 ml of water and this was extracted with two 100 ml portions of cyclohexane. The organic layers were combined and dried over $MgSO_4$. The dried extracts were combined with the filtrate obtained from the reaction mixture and the solvent was removed under reduced pressure. The product was a clear yellowish viscous oil weighing 288.

EVALUATION OF PRODUCTS

Demulsifying Test

The test was run in accordance with ANSI/ASTM D2711-74.

Formulations using the product of Example 2 were prepared with a 150" (210° F.) solvent paraffinic bright mineral oil containing 2% of an emulsifier. Emulsions were prepared from 77% by weight of such formulation in water. The following table summarizes the demulsifying capabilities of the product at various concentrations:

TABLE 1

| % By Wt. of Product of Example 2 | 0 | 0.02 | 0.05 | 0.08 | 0.10 |
|---|---|---|---|---|---|
| Demulsibility | | | | | |
| % $H_2O$ in oil | 9.0 | 10 | Trace | Trace | 0 |
| Free $H_2O$, ml. | 61 | 59 | 87 | 90 | 91 |
| Emulsion, ml. | 91 | 91 | Trace | 0 | 0 |

Shell 4-Ball Test

The products of the Examples were tested in the 4-Ball Test using a modified 4-Ball machine. In this test, three stationary balls are placed in a lubricant cup and a lubricant containing the additive to be tested is added thereto. A fourth ball is placed on a chuck mounted on a device which can be used to spin the ball at known speeds and loads.

One percent by weight of each product was placed in a blend of a 150" (210° F.) solvent paraffinic bright mineral oil and a 200" (100° F.) solvent paraffinic neutral mineral oil. These were blended in a ratio of 80/20, respectively. The samples were tested at various temperatures and speeds, but always at a load of 60 kg and for 30 minutes. The following table summarizes the test results, Table 2 showing results with the oil containing no product.

TABLE 2

| | Room Temperature | | | | 200° F. | | | | 390° F. | | | |
|---|---|---|---|---|---|---|---|---|---|---|---|---|
| RPM | 500 | 1000 | 1500 | 2000 | 500 | 1000 | 1500 | 2000 | 500 | 1000 | 1500 | 2000 |
| Example 1 | | | | | | | | | | | | |
| Average Scar Diameter* | | | | | | | | | | | | |
| Horizontal | 0.40 | 1.50 | 0.50 | 0.70 | 0.50 | 0.50 | 0.50 | 2.40 | 0.50 | 1.80 | 0.60 | 2.20 |
| Vertical | 0.40 | 1.50 | 0.50 | 0.70 | 0.50 | 0.50 | 0.50 | 2.40 | 0.50 | 1.80 | 0.60 | 2.20 |
| Example 2 | | | | | | | | | | | | |
| Average Scar Diameter* | | | | | | | | | | | | |
| Horizontal | 0.40 | 0.40 | 0.60 | 2.50 | 0.50 | 0.50 | 0.60 | 2.37 | 0.80 | 1.60 | 2.30 | 2.00 |
| Vertical | 0.40 | 0.50 | 0.60 | 2.50 | 0.50 | 0.50 | 0.60 | 2.37 | 0.80 | 1.60 | 2.30 | 2.00 |
| Untreated Oil | | | | | | | | | | | | |
| Average Scar | | | | | | | | | | | | |

TABLE 2-continued

| | Room Temperature | | | | 200° F. | | | | 390° F. | | | |
|---|---|---|---|---|---|---|---|---|---|---|---|---|
| RPM | 500 | 1000 | 1500 | 2000 | 500 | 1000 | 1500 | 2000 | 500 | 1000 | 1500 | 2000 |
| Diameter* | | | | | | | | | | | | |
| Final Average | 0.50 | 0.60 | 0.883 | 2.34 | 0.60 | 1.06 | 1.86 | 2.23 | 1.00 | 1.31 | 2.06 | 1.98 |

*in millimeters

I claim:

1. A reaction product made by the steps of (1) forming a partial ester of a polyhydric alcohol with a monocarboxylic acid, wherein the acid is present to the extent of at least 1 mole thereof per mole of the alcohol, but less than the amount required to react with all the alcohol hydroxyls, and (2) reacting the material of (1) with from about 0.25 mole to about 3.0 moles per mole of (1) of a phosphorus oxyhalide or a trihydrocarbyl phosphate.

2. The product of claim 1 wherein the polyhydric alcohol contains from 2 to 20 carbon atoms and from 2 to 12 hydroxyls.

3. The product of claim 2 wherein the alcohol contains 2 to 6 carbon atoms.

4. The product of claim 2 wherein the alcohol contains 2 to 4 carbon atoms.

5. The product of claim 1 wherein the acid contains 4 to 20 carbon atoms.

6. The product of claim 5 wherein the acid contains 5 to 9 carbon atoms or mixtures thereof.

7. The product of claim 1 wherein the phosphorus oxyhalide is phosphorus oxychloride.

8. The product of claim 1 wherein the phosphate is triethyl phosphate.

9. A lubricant composition comprising a lubricant and an antiwear or demulsifying amount of the product of claim 1.

10. The composition of claim 9 wherein the polyhydric alcohol contains from 2 to 20 carbon atoms and from 2 to 12 hydroxyls.

11. The composition of claim 10 wherein the alcohol contains 2 to 6 carbon atoms.

12. The composition of claim 10 wherein the alcohol contains 2 to 4 carbon atoms.

13. The composition of claim 9 wherein the acid contains 4 to 20 carbon atoms.

14. The composition of claim 13 wherein the acid contains 5 to 9 carbon atoms or mixtures thereof.

15. The composition of claim 9 wherein the phosphorus oxyhalide is phosphorus oxychloride.

16. The composition of claim 9 wherein the phosphate is triethyl phosphate.

* * * * *